United States Patent [19]

Kisida et al.

[11] Patent Number: 4,612,323
[45] Date of Patent: Sep. 16, 1986

[54] INSECTICIDAL AND ACARICIDAL DERIVATIVES OF 1-BENZYLBENZIMIDAZOLE

[75] Inventors: Hirosi Kisida, Takarazuka; Toshihiko Yano, Ikoma, both of Japan

[73] Assignee: Sumitomo Chemical Company, Limited, Osaka, Japan

[21] Appl. No.: 619,178

[22] Filed: Jun. 11, 1984

[30] Foreign Application Priority Data

Jun. 27, 1983 [JP] Japan .................. 58-116744
Jan. 30, 1984 [JP] Japan .................. 59-16595

[51] Int. Cl.⁴ .................. A01N 43/52; C07D 235/08
[52] U.S. Cl. .................. 514/394; 548/325; 548/327
[58] Field of Search .................. 548/325, 327, 333; 424/273 R; 514/394

[56] References Cited

U.S. PATENT DOCUMENTS

| 4,046,773 | 9/1977  | Andriska et al. | 548/341 |
| 4,118,487 | 10/1978 | Regel et al.    | 548/335 |
| 4,179,277 | 12/1979 | Beck et al.     | 548/337 |
| 4,238,405 | 12/1980 | Felix           | 514/383 |
| 4,251,512 | 2/1981  | Brandes et al.  | 548/337 |
| 4,359,469 | 11/1982 | Stetter et al.  | 548/341 |

Primary Examiner—Richard A. Schwartz
Assistant Examiner—Kurt G. Briscoe
Attorney, Agent, or Firm—Birch, Stewart, Kolasch & Birch

[57] ABSTRACT

An insecticidal and/or acaricidal composition which comprises as an active ingredient an effective amount of a benzimidazole derivative of the formula:

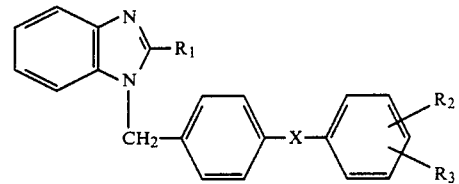

wherein $R_1$ is a hydrogen atom or a lower alkyl group, $R_2$ and $R_3$ are, the same or different, each a hydrogen atom, a halogen atom, a nitro group, a cyano group or an optionally substituted lower alkyl, lower alkenyl, lower alkynyl, cyclo(lower)alkyl, lower alkoxy, lower alkenyloxy, lower alkynyloxy, cyclo(lower)alkoxy, lower alkylthio, lower alkenylthio, lower alkynylthio, cyclo(lower)alkylthio, di(lower)alkylamino, lower alkylsulfonyl or lower alkylsulfinyl group, or $R_2$ and $R_3$ are combined together to form an optionally substituted 5- or 6-membered, saturated or unsaturated ring optionally having not more than two oxygen atoms or sulfur atoms within the ring and X is an oxygen atom, a sulfur atom, a methylene group, a sulfonyl group, a sulfinyl group or an imino group, and an inert carrier or diluent.

19 Claims, No Drawings

INSECTICIDAL AND ACARICIDAL DERIVATIVES OF 1-BENZYLBENZIMIDAZOLE

The present invention relates to benzimidazole derivatives. More particularly, it relates to benzimidazole derivatives (hereinafter referred to as "benzimidazole(s) (I)") of the formula:

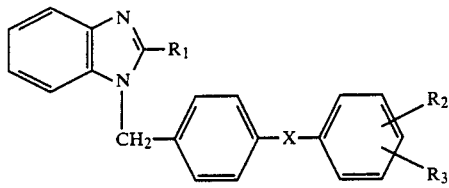

wherein $R_1$ is a hydrogen atom or a lower alkyl group, $R_2$ and $R_3$ are, the same or different, each a hydrogen atom, a halogen atom, a nitro group, a cyano group or an optionally substituted lower alkyl, lower alkenyl, lower alkynyl, cyclo(lower)alkyl, lower alkoxy, lower alkenyloxy, lower alkynyloxy, cyclo(lower)alkoxy, lower alkylthio, lower alkenylthio, lower alkynylthio, cyclo(lower)alkylthio, di(lower)alkylamino, lower alkylsulfonyl or lower alkylsulfinyl group, or $R_2$ and $R_3$ are combined together to form an optionally substituted 5- or 6-membered, saturated or unsaturated ring optionally having not more than two oxygen atoms or sulfur atoms within the ring, X is an oxygen atom, a sulfur atom, a methylene group, a sulfonyl group, a sulfinyl group or an imino group, and their production and use as insecticides and/or acaricides.

The term "lower" as hereinabove used is intended to mean usually a group having not more than 12 carbon atoms, preferably not more than 8 carbon atoms. More preferably, $R_2$ and $R_3$ represent each a hydrogen atom, a halogen atom, a $C_1$-$C_8$ alkyl group, a $C_2$-$C_6$ alkenyl group, a $C_2$-$C_6$ alkynyl group, a cyclo($C_3$-$C_6$)alkyl group, a $C_1$-$C_6$ alkoxy group, a $C_2$-$C_6$ alkenyloxy group, a $C_2$-$C_6$ alkynyloxy group, a cyclo($C_3$-$C_6$)alkyloxy group, a $C_1$-$C_6$ alkylthio group, a $C_2$-$C_6$ alkenylthio group, a $C_2$-$C_6$ alkynylthio group, a cyclo($C_3$-$C_6$)alkylthio group, a di($C_1$-$C_6$)alkylamino group, a $C_1$-$C_6$ alkylsulfonyl group, a $C_1$-$C_6$ alkylsulfinyl group, a halo($C_1$-$C_6$)alkyl group, a halo($C_2$-$C_6$)alkenyl group, a halo($C_2$-$C_6$)alkynyl group, a halo($C_1$-$C_6$)alkoxy group, a halo($C_2$-$C_6$)alkenyloxy group, a halo($C_2$-$C_6$)alkynyloxy group, a halo($C_1$-$C_6$)alkylthio group, a halo($C_2$-$C_6$)alkenylthio group, a halo($C_2$-$C_6$)alkynylthio group, a halo($C_1$-$C_6$)alkylsulfonyl group, a halo($C_1$-$C_6$)alkylsulfinyl group, a $C_1$-$C_5$ alkoxy($C_1$-$C_5$)alkyl group, a halo($C_1$-$C_5$)alkoxy($C_1$-$C_5$)alkyl group, a $C_1$-$C_5$ alkylthio($C_1$-$C_5$)alkyl group, a halo($C_1$-$C_5$)alkylthio($C_1$-$C_5$)alkyl group, a $C_1$-$C_5$alkoxy($C_1$-$C_5$)alkoxy group, a halo($C_1$-$C_5$)alkoxy($C_1$-$C_5$)alkoxy group, a $C_2$-$C_5$ alkenyloxy($C_1$-$C_4$)alkyl group, a $C_2$-$C_5$ alkynyloxy($C_1$-$C_4$)alkyl group, a $C_2$-$C_5$ alkenyloxy($C_1$-$C_4$)alkoxy group, a $C_2$-$C_5$ alkynyloxy($C_1$-$C_4$)alkoxy group, a $C_1$-$C_5$ alkoxy($C_1$-$C_5$)alkylthio group, a $C_1$-$C_5$ alkylthio($C_1$-$C_5$)alkylthio group, a $C_1$-$C_5$ alkylthio($C_1$-$C_5$)alkoxy group, a 3,4-methylenedioxy group, a 3,4-difluoromethylenedioxy group, a 3,4-trifluoroethylenedioxy group, a 3,4-trimethylene group, a 3,4-tetramethylene group, etc. In these specific groups, however, the total carbon number in such group as including two carbon chain moieties will be from 2 to 6.

Among the benzimidazoles (I), preferred are those wherein $R_1$ is a hydrogen atom or a methyl group, $R_2$ and $R_3$ are, the same or different, each a hydrogen atom, a halogen atom, a $C_1$-$C_6$ alkyl group, a $C_1$-$C_6$ alkoxy group or a $C_1$-$C_6$ alkylthio group and X is an oxygen atom, a sulfur atom, a methylene group or a sulfonyl group.

Hitherto, it has been known that some kinds of benzimidazole derivatives such as 1-(3,7-dimethylocta-2,6-dienyl)benzimidazole show an insecticidal activity against house flies (Agric.Biol.Chem., 46 (6) 1715 (1982)). However, their insecticidal effect is not sufficient.

It has now been found that the benzimidazoles (I) of the invention exert an excellent insecticidal activity against Diptera (e.g. common mosquito, yellow fever mosquito). It has also been found that they show a prominent acaricidal activity against Tetranychidae (e.g. carmine spider mite, two-spotted spider mite, citrus red mite). Advantageously, their acaricidal activity is effective for Tetranhchidae having resistance to conventional acaricides. The benzimidazoles (I) are thus useful as the active ingredients for agricultural insecticides, agricultural acaricides, sanitary insecticides, etc.

The benzimidazoles (I) of the invention can be prepared by reacting a benzimidazole compound of the formula:

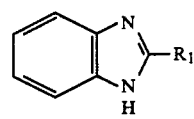

wherein $R_1$ is as defined above with a benzyl compound of the formula:

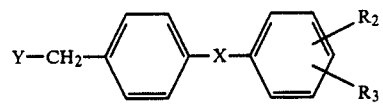

wherein $R_2$, $R_3$ and X are each as defined above and Y is a leaving group such as a halogen atom, a tosyloxy group or a mesyloxy group in the existence of an acid binding agent.

The molar ratio of the benzimidazole compound (II) and the benzyl compound (III) is usually 1:0.1–10, preferably 1:0.8–1.0. The molar ratio of the benzimidazole compound (II) and the acid binding agent may be ordinarily 1:0.9–1.1.

Examples of the acid binding agent are alkali metals (e.g. lithium, sodium, potassium), alkali metal hydrides (sodium hydride, potassium hydride), alkali metal amides (e.g. sodium amide), alkali metal hydroxides (e.g. sodium hydroxide, potassium hydroxide), alkali metal carbonates (e.g. sodium carbonate, potassium carbonate), organic bases (e.g. triethylamine, N,N-dimethylaniline), etc.

The reaction may be carried out in the presence or absence of an inert solvent, preferably in the presence of an inert solvent. The reaction is generally effected at a temperature of −30° C. to the boiling temperature of the reaction mixture, preferably from 0° to 110° C. The reaction is usually accomplished within a period of 0.5 to 50 hours.

Examples of the inert solvent are water, hydrocarbons (e.g. benzene, toluene, xylene), ethers (e.g. diethyl ether, diisopropyl ether, dioxane, tetrahydrofuran, ethylene glycol dimethyl ether, dimethoxyethane), ketones (e.g. acetone, methylethylketone, methylisobutylketone, cyclohexanone), acid amides (e.g. dimethylformamide, diethylformamide, dimethylacetamide), sulfoxides (e.g. dimethylsulfoxide), or their mixtures.

In order to accelerate the reaction, a phase transfer catalyst such as benzyltriethylammonium chloride or tetrabutylammonium bromide may be employed.

Recovery of the benzimidazole (I) from the reaction mixture may be effected in a conventional manner for post-treatment. When desired, the recovered benzimidazole (I) may be purified in a per se conventional procedure such as chromatography, distillation or recrystallization.

The benzimidazoles (I) of the invention can form salts with acids, and those salts are also included within the scope of the invention. Examples of the acid are inorganic acids (e.g. hydrochloric acid, sulfuric acid), organic acids (e.g. trifluoroacetic acid), etc.

As the benzimidazole compound (II), there may be exemplified benzimidazole, 2-methylbenzimidazole, 2-ethylbenzimidazole, etc.

The benzyl compound (III) is per se known or may be prepared by a conventional process. Examples of the benzyl compound (III) are 4-phenoxybenzyl bromide, 4-(3-tolyloxy)benzyl chloride, 4-(4-n-pentylphenoxy)benzyl chloride, 4-(4-ethoxyphenoxy)benzyl chloride, 4-(3-ethoxyphenoxy)benzyl chloride, 4-(4-methylthiophenoxy)benzyl chloride, 4-benzoylbenzyl bromide, 4-(4-vinyloxyphenoxy)benzyl chloride, 4-(3-chlorophenoxy)benzyl chloride, 4-(2-fluorophenoxy)benzyl p-toluenesulfonate, 4-(3-fluorophenoxy)benzyl bromide, 4-(3-isopropylphenoxy)benzyl chloride, 4-(4-ethynylphenoxy)benzyl chloride, 4-(3-n-propylthiophenoxy)benzyl chloride, 4-(4-methanesulfonylphenoxy)benzyl chloride, 4-(3-trifluoromethylphenoxy)benzyl bromide, 4-(4-cyclopropylphenoxy)benzyl chloride, 4-(2-chlorophenylthio)benzyl bromide, 4-(3-bromophenoxy)benzyl bromide, 4-(4-ethylphenoxy)benzyl chloride, 4-(3-ethylphenoxy)benzyl chloride, 4-(3-N,N-dimethylaminophenoxy)benzyl bromide, 4-(3-n-propoxyphenoxy)benzyl chloride, 4-(3-n-butoxyphenoxy)benzyl chloride, 4-(3-n-pentyloxyphenoxy)benzyl chloride, 4-(4-isopropylthiophenoxy)benzyl chloride, 4-[4-(2,2-dichlorovinyl)phenoxy]benzyl chloride, 4-(3-n-propylphenoxy)benzyl chloride, 4-(4-isopropylphenoxy)benzyl chloride, 4-benzylbenzyl methanesulfonate, 4-(3-ethylthiophenoxy)benzyl chloride, 4-(4-methoxymethylphenoxy)benzyl chloride, 4-(4-n-butylthiophenoxy)benzyl chloride, 4-(4-difluoromethoxyphenoxy)benzyl chloride, 4-(4-n-propylphenoxy)benzyl chloride, 4-(4-n-butylphenoxy)benzyl chloride, 4-(3-vinylphenoxy)benzyl chloride, 4-(4-allylphenoxy)benzyl chloride, 4-(4-n-propoxyphenoxy)benzyl chloride, 4-(4-sec-butylphenoxy)benzyl chloride, 4-(2,5-dimethylphenoxy)benzyl chloride, 4-(2,3-dimethylphenoxy)benzyl chloride, 4-(3,5-difluorophenoxy)benzyl chloride, 4-(4-n-butoxyphenoxy)benzyl chloride, 4-(4-n-pentylthiophenoxy)benzyl chloride, 4-(3,4-methylenedioxyphenoxy)benzyl chloride, 4-(4-allylthiophenoxy)benzyl chloride, 4-(3-allyl-oxyphenoxy)benzyl chloride, 4-(4-propargyloxyphenoxy)benzyl chloride, 4-(4-n-hexylphenoxy)benzyl chloride, 4-[4-(2-butenyl)phenoxy]benzyl chloride, 4-[4-(1-methylallyl)phenoxy]benzyl chloride, 4-(3-n-hexyloxyphenoxy)benzyl chloride, 4-(3-isopropoxyphenoxy)benzyl chloride, 4-[4-(1-methylcyclopropyl)phenoxy]benzyl chloride, 4-(3-ethynyloxyphenoxy)benzyl chloride, 4-(4-allylthiophenoxy)benzyl chloride, 4-[4-(2,2-dichlorovinyloxy)phenoxy]benzyl chloride, 4-[4-(2-chloroallyl)phenoxy]benzyl chloride, 4-[4-(1,1,2,2-tetrafluoroethoxy)phenoxy]benzyl chloride, 4-(3-chloro-4-methylphenoxy)benzyl chloride, 4-(3,4-difluoromethylenedioxyphenoxy)benzyl chloride, 4-(4-secpentylphenoxy)benzyl chloride, 4-[4-(2-methylallyl)phenoxy]benzyl chloride, 4-[4-(2-chloroethynyl)phenoxy]benzyl chloride, 4-(4-methoxymethylthiophenoxy)benzyl chloride, 4-[4-(2,2,2-trifluoroethoxy)phenoxy]benzyl chloride, 4-(4-ethoxymethylphenoxy)benzyl chloride, 4-(3-trifluoromethylthiophenoxy)benzyl chloride, 4-(3-methoxy-4-methylphenoxy)benzyl chloride, 4-(4-propargylphenoxy)benzyl chloride, 4-(4-ethyl-2-methylphenoxy)benzyl chloride, 4-(2-methyl-4-n-propylphenoxy)benzyl chloride, 4-(4-n-butyl-2-methylphenoxy)benzyl chloride, 4-[4-(1-methyl-2-butenyl)phenoxy]benzyl chloride, 4-(3-methoxyphenoxy)benzyl chloride, 4-(4-isopropoxyphenoxy)benzyl chloride, 4-(4-sec-butoxyphenoxy)benzyl chloride, 4-(4-n-pentyloxyphenoxy)benzyl chloride, 4-[4-(1-ethoxyethyl)phenoxy]benzyl chloride, 4-(3-allylthiophenoxy)benzyl chloride, 4-(4-cyclopropylthiophenoxy)benzyl chloride, 4-(3-allyloxymethylphenoxy)benzyl chloride, 4-(4-ethoxyphenylthio)benzyl chloride, 4-(3-ethynyloxymethylphenoxy)benzyl chloride, 4-(4-methylthiomethylthiophenoxy)benzyl chloride, 4-(4-isobutylthiophenoxy)benzyl chloride, 4-[4-(2-methylallyloxy)phenoxy]benzyl chloride, 4-(3-ethanesulfonylphenoxy)benzyl chloride, 4-[4-(1,1-dichloro-2,2-difluoroethoxy)phenoxy]benzyl chloride, 4-(2-methyl-4-n-propoxyphenoxy)benzyl chloride, 4-(2-chloro-4-ethoxyphenoxy)benzyl chloride, 4-[4-(2-butenyloxy)phenoxy]benzyl chloride, 4-[4-(1-methylallyloxy)phenylthio]benzyl chloride, 4-(3-ethoxyanilino)benzyl chloride, 4-(5,6,7,8-tetrahydro-2-naphthyloxy)benzyl chloride, 4-(4-bromo-3-chlorophenoxy)benzyl chloride, 4-(4-trifluoromethylphenoxy)benzyl chloride, 4-benzenesulfinylbenzyl chloride, 4-(3-nitrophenoxy)benzyl chloride, 4-(4-n-propoxyphenoxy)benzyl chloride, 4-(4-methoxyphenoxy)benzyl chloride, 4-(4-ethylthiophenoxy)benzyl chloride, 4-(4-n-propylthiophenoxy)benzyl chloride, 4-(3-methylthiophenoxy)benzyl chloride, 4-(3-n-butylthiophenoxy)benzyl chloride, 4-(4-n-propoxyphenylthio)benzyl chloride, 4-(4-ethylbenzoyl)benzyl chloride, 4-(2,3-dihydrobenzofuran-5-yloxy)benzyl chloride, 4-(2,3-dihydro-2,2-dimethylbenzofuran-5-yloxy)benzyl chloride, 4-(indan-5-yloxy)benzyl chloride, 4-[4-(2,2,3-trifluoroethoxy)phenoxy]benzyl chloride, 4-[4-(2-bromo-1,1,2,2-tetrafluoroethoxy)phenoxy]benzyl chloride, etc.

Practical and presently preferred embodiments for preparation of the benzimidazole (I) are illustratively shown in the following Examples.

EXAMPLE 1

To a suspension of sodium hydride (0.14 g, 3.6 mmole; 62% in oil) in anhydrous dimethylformamide (10 ml), 2-methylbenzimidazole (0.48 g, 3.6 mmole) was added while stirring, and stirring was continued at room temperature for 1 hour. The resultant mixture was cooled to 5°–10° C., and a solution of 4-(3-tolyloxy)benzyl bromide (1.00 g, 3.6 mmole) in anhydrous dimethylformamide (5 ml) was dropwise added thereto in 30 minutes, followed by stirring at room temperature overnight. After completion of the reaction, the reaction mixture was poured into water (100 ml) and extracted with toluene (30 ml) two times. The toluene layer was washed with water, dried over anhydrous sodium sulfate and distilled under reduced pressure to remove toluene. The residue was purified by silica gel column chromatography to give 2-methyl-1-[4-(3-tolyloxy)benzyl]benzimidazole (0.84 g) as colorless liquid. $n_D^{27.0}$ 1.6112.

EXAMPLE 2

A mixture of toluene (20 ml), 2-methylbenzimidazole (0.55 g, 4.2 mmole), triethylamine (0.42 g, 4.2 mmole) and 4-(4-ethoxyphenoxy)benzyl chloride (1.00 g, 3.8 mmole) was heated under reflux for 5 hours and then cooled to room temperature. The resultant mixture was washed with water, dried over anhydrous sodium sulfate and distilled under reduced pressure to remove toluene. The residue was purified by silica gel column chromatography to give 1-[4-(4-ethoxyphenoxy)benzyl]-2-methylbenzimidazole (1.20 g) as colorless liquid. $n_D^{26.0}$ 1.5984.

In the same manner as above, there were prepared the benzimidazoles (I) as shown in Table 1.

TABLE 1

| Compound No. | $R_1$ | $R_2$ | $R_3$ | X | Physical constant |
|---|---|---|---|---|---|
| 1 | H | H | H | O | M.P. 91.1° C. |
| 2 | H | 4-Cl | H | O | M.P. 116.8° C. |
| 3 | H | 3-Cl | H | O | $n_D^{22.5}$ 1.6275 |
| 4 | H | 2-Cl | H | O | M.P. 96.5° C. |
| 5 | H | 3-F | H | O | M.P. 73.5° C. |
| 6 | H | 2-F | H | O | M.P. 121.1° C. |
| 7 | H | 4-Br | H | O | $n_D^{23.5}$ 1.6307 |
| 8 | H | 4-$CH_3$ | H | O | M.P. 209.7° C. |
| 9 | H | 3-$CH_3$ | H | O | $n_D^{24.5}$ 1.6168 |
| 10 | H | 2-$CH_3$ | H | O | M.P. 101.5° C. |
| 11 | H | 4-$C_2H_5$ | H | O | $n_D^{21.0}$ 1.6057 |
| 12 | H | 4-n-$C_3H_7$ | H | O | $n_D^{22.0}$ 1.6805 |
| 13 | H | 4-$OCH_3$ | H | O | $n_D^{22.0}$ 1.6218 |
| 14 | H | 4-$SCH_3$ | H | O | $n_D^{24.0}$ 1.6585 |
| 15 | H | 4-$CF_3$ | H | O | $n_D^{24.5}$ 1.5783 |
| 16 | H | 3-$CF_3$ | H | O | $n_D^{26.5}$ 1.5848 |
| 17 | H | 3-Cl | 4-Cl | O | $n_D^{25.0}$ 1.6285 |
| 18 | H | 3-Cl | 5-Cl | O | M.P. 109.6° C. |
| 19 | H | 3-F | 5-F | O | M.P. 76.0° C. |
| 20 | H | 4-O—n-$C_3H_7$ | H | O | $n_D^{25.5}$ 1.6061 |
| 21 | H | 2-$CH_3$ | 3-$CH_3$ | O | M.P. 107.9° C. |
| 22 | H | 2-$CH_3$ | 5-$CH_3$ | O | $n_D^{25.0}$ 1.6127 |
| 23 | H | 3-O—$CH_2CH=CH_2$ | H | O | $n_D^{22.0}$ 1.6235 |
| 24 | H | H | H | S | $n_D^{23.5}$ 1.6570 |
| 25 | H | H | H | NH | $n_D^{25.5}$ 1.6085 |
| 26 | H | H | H | $CH_2$ | $n_D^{24.0}$ 1.6200 |
| 27 | H | H | H | SO | $n_D^{28.0}$ 1.6621 |
| 28 | H | H | H | $SO_2$ | M.P. 173.8° C. |
| 29 | $CH_3$ | H | H | O | M.P. 145.1° C. |
| 30 | $CH_3$ | 2-$CH_3$ | H | O | M.P. 102.1° C. |
| 31 | $CH_3$ | 3-$CH_3$ | H | O | $n_D^{27.0}$ 1.6112 |
| 32 | $CH_3$ | 4-$CH_3$ | H | O | M.P. 118.9° C. |
| 33 | $CH_3$ | 2-$CH_3$ | 5-$CH_3$ | O | $n_D^{25.0}$ 1.6135 |
| 34 | $CH_3$ | 3-$CH_3$ | 4-$CH_3$ | O | $n_D^{22.5}$ 1.6604 |
| 35 | $CH_3$ | 3-$CH_3$ | 5-$CH_3$ | O | M.P. 115.6° C. |
| 36 | $CH_3$ | 3-$C_2H_5$ | H | O | $n_D^{25.0}$ 1.6073 |
| 37 | $CH_3$ | 4-$C_2H_5$ | H | O | $n_D^{25.5}$ 1.6045 |
| 38 | $CH_3$ | 4-n-$C_3H_7$ | H | O | $n_D^{19.5}$ 1.5969 |
| 39 | $CH_3$ | 3-i-$C_3H_7$ | H | O | $n_D^{21.0}$ 1.6034 |
| 40 | $CH_3$ | 4-i-$C_3H_7$ | H | O | $n_D^{25.5}$ 1.6054 |
| 41 | $CH_3$ | 3-Cl | H | O | $n_D^{22.0}$ 1.6297 |
| 42 | $CH_3$ | 4-Cl | H | O | $n_D^{26.0}$ 1.6171 |
| 43 | $CH_3$ | 3-Br | H | O | $n_D^{25.5}$ 1.6325* |
| 44 | $CH_3$ | 2-F | H | O | $n_D^{24.5}$ 1.6452 |
| 45 | $CH_3$ | 3-F | H | O | $n_D^{22.0}$ 1.6045 |
| 46 | $CH_3$ | 3-F | 5-F | O | $n_D^{22.0}$ 1.5968 |
| 47 | $CH_3$ | 3-$OCH_3$ | H | O | $n_D^{25.0}$ 1.6264 |
| 48 | $CH_3$ | 4-$OCH_3$ | H | O | $n_D^{27.0}$ 1.6051 |
| 49 | $CH_3$ | 3-$OC_2H_5$ | H | O | $n_D^{22.0}$ 1.6190 |
| 50 | $CH_3$ | 4-$OC_2H_5$ | H | O | $n_D^{26.0}$ 1.5984 |
| 51 | $CH_3$ | 3-O—n-$C_3H_7$ | H | O | $n_D^{24.5}$ 1.6073 |
| 52 | $CH_3$ | 4-O—n-$C_3H_7$ | H | O | $n_D^{24.5}$ 1.5931 |
| 53 | $CH_3$ | 4-$SCH_3$ | H | O | $n_D^{22.5}$ 1.6410 |
| 54 | $CH_3$ | 3-$CF_3$ | H | O | $n_D^{23.5}$ 1.5782 |
| 55 | $CH_3$ | 4-$CF_3$ | H | O | $n_D^{22.0}$ 1.5751 |
| 56 | $CH_3$ | 3-$NO_2$ | H | O | $n_D^{22.5}$ 1.6211 |
| 57 | $CH_3$ | 3-$CH_3$ | 4-Cl | O | $n_D^{20.5}$ 1.6173 |
| 58 | $CH_3$ | 3,4-(O—$CH_2$—O)- | | O | $n_D^{24.0}$ 1.6099 |
| 59 | $CH_3$ | 3,4-[$CH_2$-($CH_2$)$_2$-$CH_2$]- | | O | $n_D^{25.5}$ 1.6193 |
| 60 | $C_2H_5$ | H | H | O | $n_D^{23.5}$ 1.6275 |
| 61 | $C_2H_5$ | 3-Cl | H | O | $n_D^{22.5}$ 1.6315 |
| 62 | $C_2H_5$ | 3-$CH_3$ | H | O | $n_D^{22.5}$ 1.6067 |
| 63 | $C_2H_5$ | 4-$OC_2H_5$ | H | O | $n_D^{24.5}$ 1.5915 |
| 64 | $C_2H_5$ | 4-$OCH_3$ | H | O | $n_D^{22.5}$ 1.5982 |
| 65 | n-$C_3H_7$ | 4-Cl | H | O | $n_D^{26.5}$ 1.6085 |
| 66 | iso-$C_3H_7$ | 4-Cl | H | O | $n_D^{26.0}$ 1.6070 |

TABLE 1-continued

| Compound No. | $R_1$ | $R_2$ | $R_3$ | X | Physical constant |
|---|---|---|---|---|---|
| 67 | $CH_3$ | 4-n-$C_4H_9$ | H | O | $n_D^{24.5}$ 1.5934 |
| 68 | $CH_3$ | 4-n-$C_5H_{11}$ | H | O | $n_D^{24.5}$ 1.5942 |
| 69 | $CH_3$ | 3-O-n-$C_4H_9$ | H | O | $n_D^{22.5}$ 1.6028 |
| 70 | $CH_3$ | 4-O-n-$C_4H_9$ | H | O | $n_D^{24.5}$ 1.5925 |
| 71 | $CH_3$ | 4-O-n-$C_5H_{11}$ | H | O | $n_D^{24.5}$ 1.5892 |
| 72 | $CH_3$ | 4-O-n-$C_6H_{13}$ | H | O | $n_D^{20.5}$ 1.5900 |
| 73 | $CH_3$ | 3-O-$CH_2CH=CH_2$ | H | O | $n_D^{24.0}$ 1.6183 |
| 74 | $CH_3$ | mixture (3:2) of 3-O-$CH_2C\equiv CH$ 3-O-$CH=C=CH_2$ | H | O | $n_D^{24.0}$ 1.6263 |
| 75 | $CH_3$ | 4-$SO_2CH_3$ | H | O | M.P. 161.1° C. |
| 76 | H | 3,4-(-O-$CH_2$-O-) | | O | M.P. 108.4° C. |
| 77 | H | 4-n-$C_4H_9$ | H | O | $n_D^{24.3}$ 1.6025 |
| 78 | H | 4-n-$C_5H_{11}$ | H | O | $n_D^{24.0}$ 1.5947 |
| 79 | H | 4-O-n-$C_4H_9$ | H | O | M.P. 50-53° C. |
| 80 | H | 3-O-n-$C_5H_{11}$ | H | O | $n_D^{21.5}$ 1.5980 |
| 81 | H | 2-Cl | H | S | $n_D^{28.0}$ 1.6647 |
| 82 | $CH_3$ | 4-S-n-$C_3H_7$ | H | O | $n_D^{24.5}$ 1.6254 |
| 83 | $CH_3$ | 4-$SC_2H_5$ | H | O | $n_D^{21.0}$ 1.6267 |
| 84 | $CH_3$ | 4-$OCHF_2$ | H | O | $n_D^{23.0}$ 1.5952 |
| 85 | H | 4-n-$C_6H_{13}$ | H | O | $n_D^{25.0}$ 1.5921 |
| 86 | $CH_3$ | 4-n-$C_8H_{17}$ | H | O | $n_D^{24.5}$ 1.5678 |
| 87 | $CH_3$ | 4-n-$C_6H_{13}$ | H | O | $n_D^{24.5}$ 1.5845 |
| 88 | $CH_3$ | 4-O-$CH_2CH=CH_2$ | H | O | $n_D^{24.5}$ 1.6057 |

*M.P. 115.9° C. (crystallized after being allowed for one week).

Regarding the application of the benzimidazoles (I) as insecticidal and/or acaricidal agents, they may be used as such or in the form of appropriate compositions such as emulsifiable concentrates, wettable powders, dusts, granules, oils, aerozoles, heating or non-heating fumigants, sprays, baits, etc. The content of the benzimidazoles (I) in such compositions is usually from about 0.01 to 95% by weight.

The composition can be formulated in a per se conventional manner by mixing at least one of the benzimidazoles (I) with an appropriate solid, liquid or gaseous carrier(s) or diluent(s). An appropriate adjuvant(s) (e.g. surfactants, adherents, dispersants, stabilizers) may be also admixed therein for improving the dispersibility and other properties of the composition.

Examples of the solid carriers or diluents are kaolin clay, attapulgite clay, bentonite, fuller's earth, pyrophyllite, talc, diatomaceous earth, calcite, corn stem powders, walnut-shell powders, fine powders or granules of urea, ammonium sulfate or synthetic hydrated silica, etc. Examples of the liquid carriers or diluents are aliphatic hydrocarbons (e.g. kerosene, lamp oil), aromatic hydrocarbons (e.g. benzene, toluene, xylene, methylnaphthalene), halogenated hydrocarbons (e.g. dichloroethane, trichloroethylene, carbon tetrachloride), alcohols (e.g. methanol, ethanol, isopropanol, ethylene glycol, cellosolve), ketones (e.g. acetone, methyl ethyl ketone, cyclohexanone, isophorone), ethers (e.g. diethyl ether, dioxane, tetrahydrofuran), esters (e.g. ethyl acetate), nitriles (e.g. acetonitrile, isobutylonitrile), acid amides (e.g. dimethylformamide, dimethylacetamide), dimethylsulfoxide, botanical oils (e.g. soybean oil, cotton-seed oil), etc. Examples of the gaseous carriers or diluents are Freon gas, liquefied petroleum gas, dimethyl ether, etc.

Examples of the surfactants used for emulsification, dispersion or spreading may be any of ionic and non-ionic types. Examples of the ionic surfactants are alkylsulfates, alkylsulfonates, arylsulfonates, dialkylsulfosuccinates, phosphates of polyoxyethylene alkylaryl ether, condensates of naphthalenesulfonic acid and formalin, etc. Examples of the non-ionic surfactants are polyoxyethylene alkyl ethers, polyoxyethylene polyoxypropylene blocked copolymers, sorbitan fatty acid esters, polyoxyethylene sorbitan fatty acid esters, etc. Examples of the adherents and dispersants may include ligninsulfonates, alginates, polyvinyl alcohol, gum arabic, mollasses, casein, gelatin, CMC (carboxymethyl cellulose), pin seed oil, agar, etc. As the stabilizers, there may be used alkyl phosphates (e.g. isopropyl acid phosphate, tricresyl phosphate), botanical oils, epoxidized oils, various surfactants, antioxidizing agents (e.g. 2,6-di-t-butyl-p-cresol, mixture of 2-t-butyl-4-methoxyphenol and 3-t-butyl-4-methoxyphenol), aliphatic acid salts (e.g. sodium oleate, calcium stearate), aliphatic acid esters (e.g. methyl oleate, methyl stearate), etc.

The benzimidazoles (I) of the invention formulated into an appropriate composition may be applied as such or in a form of dilution with water by a suitable application method such as spraying, fumigating or smoking, or in combination with animal bait.

In addition, said composition may contain other insecticides, acaricides, nematocides, fungicides, herbicides, plant growth regulators, fertilizers, soil improvers, etc.

The dosage of the benzimidazole (I) as the active ingredient in an insecticidal and/or acaricidal agent is generally from 5 to 500 grams per 10 ares. When the composition is applied as an emulsifiable concentrate or a wettable powder, the concentration of the active ingredient may be normally from 10 to 1000 ppm. In case of such formulation as dusts, granules, oils, aerosoles, etc., the composition may be applied as such without diluting with water.

Some practical embodiments of the composition for the control of insects and/or acarids according to the invention are illustratively shown in the following Formulation Examples wherein % and part(s) are by weight.

Formulation Example 1

Compound No. 1 or 29 (0.2 part), xylene (2 parts) and lamp oil (97.8 parts) are mixed well to make an oil.

Formulation Example 2

Anyone of Compound Nos. 29 to 32, 36, 37, 41 to 50, 52, 54, 55 and 60 to 66 (10 parts), polyoxyethylene styrylphenyl ether (14 parts), calcium dodecylbenzenesulfonate (6 parts) and xylene (70 parts) are mixed well to make an emulsifiable concentrate.

Formulation Example 3

Compound No. 7 or 66 (20 parts), fenitrothion (O,O-dimethyl-O-(3-methyl-4-nitrophenyl)phosphorothioate; 10 parts), calcium ligninsulfonate (3 parts), sodium laurylsulfate (2 parts) and synthetic hydrated silica (65 parts) are mixed well in a pulverizer to make a wettable powder.

Formulation Example 4

Compound No. 10 or 31 (1 part), carbaryl (1-naphthyl N-methylcarbamate; 2 parts), kaolin clay (87 parts) and talc (10 parts) are mixed well in a pulverizer to give a dust.

Formulation Example 5

Compound No. 15 or 50 (5 parts), synthetic hydrated silica (1 part), calcium ligninsulfonate (2 parts), bentonite (30 parts) and kaolin clay (62 parts) are mixed well in a pulverizer. To the resultant mixture, water is added, and the resulting mixture is kneaded well and granulated by the aid of a granulator, followed by drying to give granules.

The following Test Examples present some typical test data indicating the excellent insecticidal and acaricidal activities of the benzimidazoles (I). The compounds used for comparison are as follows:

| Compound No. | Chemical structure | Remarks |
|---|---|---|
| A | [benzimidazole with N-CH₂CH=C(CH₃)-CH₂CH₂CH=C(CH₃)₂] | Agric. Biol. Chem., 46, (6) 1715 (1982) |
| B | Cl-C₆H₃(CH₃)-N=CH-N(CH₃)₂ | Chlorodimeform |
| C | (Cl-C₆H₄)₂C(OH)(CCl₃) | Dicofol |

Test Example 1

An emulsifiable concentrate prepared as in Formulation Example 2 was diluted with water to make a concentration of 3.5 ppm. The dilution (100 ml) was charged in a plastic cup (each 180 ml volume), and twenty last instar larvae of common mosquito (*Culex pipiens pallens*) were released therein. On the next day, the rate of death was calculated. Thereafter, the feeding was continued until all the larvae in the untreated plot emerged, whereupon the rate of emergence inhibition was observed.

The rate of death and the rate of emergence inhibition were respectively determined according to the following criteria:

Rate of death a: more than 90% death
b: between 90 and 10% death
c: less than 10% death Rate of emergence inhibition a: more than 90% inhibition
b: between 90 and 80% inhibition
c: less than 80% inhibition
The results are shown in Table 2.

TABLE 2

| Compound No. | Rate of death | Rate of emergence inhibition |
|---|---|---|
| 1 | b | a |
| 2 | b | a |
| 3 | a | a |
| 4 | b | a |
| 5 | c | a |
| 6 | b | a |
| 7 | b | a |
| 8 | a | a |
| 9 | b | a |
| 10 | b | a |
| 11 | b | a |
| 13 | b | a |
| 15 | b | a |
| 17 | b | a |
| 18 | b | a |
| 19 | a | a |
| 21 | b | a |
| 24 | b | a |
| 25 | b | a |
| 26 | b | a |
| 28 | c | a |
| 29 | c | a |
| 31 | b | a |
| 41 | b | a |
| 42 | b | a |
| 43 | b | a |
| 44 | b | a |
| 45 | c | a |
| 46 | b | a |
| 50 | b | a |
| 60 | c | a |
| 61 | c | a |
| 65 | c | a |
| 66 | c | a |
| 68 | b | a |
| 74 | b | a |
| 76 | b | a |
| 84 | c | a |
| 88 | c | a |
| Untreated | c | c |

EXAMPLE 2

Adults of female carmine spider mites (*Tetranychus cinnabarinus*) were permitted to live on leaves (10 mites per leaf) of kidney bean after 7 days of its plantation in the pots, and the adults were kept at 25° C. After 6 days, a dilution (500 ppm) of the emulsifiable concentrate prepared as in Formulation Example 2 was sprayed over the pots placed on a turn table at a spray volume of 10 ml per pot, and also 2 ml of the dilution were applied to the soil in each pot. Eight days thereafter, the plant damage by the mites was observed and evaluated according to the following criteria:

—: no material damage to leaves
+: slight damage to leaves
++: same damage as seen in untreated plot
The results are shown in Table 3.

TABLE 3

| Compound No. | Plant damage |
| --- | --- |
| 1 | — |
| 2 | — |
| 3 | —~+ |
| 4 | —~+ |
| 5 | —~+ |
| 7 | — |
| 8 | —~+ |
| 9 | —~+ |
| 10 | — |
| 12 | — |
| 13 | — |
| 14 | — |
| 16 | — |
| 17 | —~+ |
| 19 | —~+ |
| 20 | — |
| 21 | — |
| 22 | — |
| 23 | — |
| 24 | — |
| 27 | — |
| 28 | —~+ |
| 29 | — |
| 30 | — |
| 31 | — |
| 32 | —~+ |
| 33 | — |
| 34 | —~+ |
| 35 | —~+ |
| 36 | —~+ |
| 37 | —~+ |
| 38 | — |
| 39 | — |
| 40 | — |
| 41 | — |
| 43 | —~+ |
| 44 | — |
| 46 | — |
| 47 | —~+ |
| 48 | — |
| 49 | —~+ |
| 50 | — |
| 51 | — |
| 52 | —~+ |
| 53 | — |
| 54 | — |
| 55 | —~+ |
| 56 | —~+ |
| 57 | — |
| 58 | — |
| 59 | — |
| 62 | —~+ |
| 63 | —~+ |
| 64 | —~+ |
| 67 | — |
| 68 | — |
| 69 | — |
| 70 | — |
| 71 | — |
| 72 | — |
| 73 | — |
| 74 | — |
| 75 | — |
| 77 | — |
| 78 | — |
| 79 | — |
| 80 | — |
| 81 | —~+ |
| 82 | — |
| 83 | — |
| 84 | — |
| 85 | — |
| 86 | — |
| 87 | — |
| 88 | — |
| A | ++ |
| B | + |
| C | —~+ |
| Untreated | ++ |

What is claimed is:

1. A benzimidazole derivative of the formula:

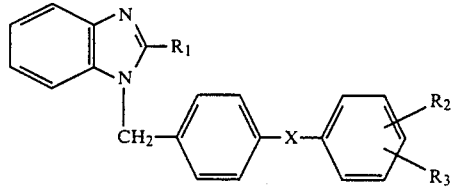

wherein $R_1$ is a hydrogen atom or a lower alkyl group, $R_2$ and $R_3$ are, the same or different, each a hydrogen atom, a halogen atom, a nitro group, a cyano group, a $C_1$-$C_8$ alkyl group, a $C_2$-$C_6$ alkenyl group, a $C_2$-$C_6$ alkynyl group, a cyclo($C_3$-$C_6$)alkyl group, a $C_1$-$C_6$ alkoxy group, a $C_2$-$C_6$ alkenyloxy group, a $C_2$-$C_6$ alkynyloxy group, a cyclo($C_3$-$C_6$)alkyloxy group, a $C_1$-$C_6$ alkylthio group, a $C_2$-$C_6$ alkenylthio group, a $C_2$-$C_6$ alkynylthio group, a cyclo($C_3$-$C_6$)alkylthio group, a di($C_1$-$C_6$)alkylamino group, a $C_1$-$C_6$ alkylsulfonyl group, a $C_1$-$C_6$ alkylsulfinyl group, a halo($C_1$-$C_6$)alkyl group, a halo($C_2$-$C_6$)alkenyl group, a halo($C_2$-$C_6$)alkynyl group, a halo($C_1$-$C_6$)alkoxy group, a halo($C_2$-$C_6$)alkenyloxy group, a halo($C_2$-$C_6$) alkynyloxy group, a halo($C_1$-$C_6$)alkylthio group, a halo($C_2$-$C_6$)alkenylthio group, a halo($C_2$-$C_6$)alkynylthio group, a halo($C_1$-$C_6$)alkylsulfonyl group, a halo($C_1$-$C_6$)alkylsulfinyl group, a $C_1$-$C_5$ alkoxy($C_1$-$C_5$)alkyl group, a halo($C_1$-$C_5$)alkoxy($C_1$-$C_5$)alkyl group, a $C_1$-$C_5$ alkylthio($C_1$-$C_5$)alkyl group, a halo($C_1$-$C_5$)alkylthio($C_1$-$C_5$)alkyl group, a $C_1$-$C_5$ alkoxy($C_1$-$C_5$)alkoxy group, a halo($C_1$-$C_5$)alkoxy($C_1$-$C_5$)alkoxy group, a $C_2$-$C_5$ alkenyloxy($C_1$-$C_4$)alkyl group, a $C_2$-$C_5$ alkynyloxy($C_1$-$C_4$)alkyl group, a $C_2$-$C_5$ alkenyloxy($C_1$-$C_4$)alkoxy group, a $C_2$-$C_5$ alkynyloxy($C_1$-$C_4$)alkoxy group, a $C_1$-$C_5$ alkoxy($C_1$-$C_5$)alkylthio group, a $C_1$-$C_5$ alkylthio($C_1$-$C_5$)alkylthio group or a $C_1$-$C_5$ alkylthio($C_1$-$C_5$)alkoxy group, or $R_2$ and $R_3$ are combined together to form a 3,4-methylenedioxy group, a 3,4-difluoromethylenedioxy group, a 3,4-trifluoroethylenedioxy group, a 3,4-trimethylene group or a 3,4-tetramethylene group and X is an oxygen atom, a sulfur atom, a methylene group, a sulfonyl group, a sulfinyl group or an imino group.

2. The benzimidazole derivative according to claim 1, wherein $R_1$ is a hydrogen atom or a methyl group.

3. The benzimidazole derivative according to claim 2, wherein X is an oxygen atom.

4. The benzimidazole derivative according to claim 1, wherein $R_1$ is a methyl group, $R_2$ is an ethoxy group at the 4-position, $R_3$ is a hydrogen atom and X is an oxygen atom.

5. The benzimidazole derivative according to claim 1, wherein $R_1$ is a methyl group, $R_2$ and $R_3$ are combined together to form a methylenedioxy ring between the 3- and 4-positions and X is an oxygen atom.

6. The benzimidazole derivative according to claim 1, wherein $R_1$ is a methyl group, $R_2$ is an ethyl group at the 4-position, $R_3$ is a hydrogen atom and X is an oxygen atom.

7. The benzimidazole derivative according to claim 1, wherein $R_1$ is a methyl group, $R_2$ is an isopropyl group at the 4-position, $R_3$ is a hydrogen atom and X is an oxygen atom.

8. The benzimidazole derivative according to claim 1, wherein $R_1$ is a methyl group, $R_2$ is a methoxy group at the 3-position, $R_3$ is a hydrogen atom and X is an oxygen atom.

9. The benzimidazole derivative according to claim 1, wherein $R_1$ is a methyl group, $R_2$ is an ethoxy group at the 3-position, $R_3$ is a hydrogen atom and X is an oxygen atom.

10. The benzimidazole derivative according to claim 1, wherein $R_1$ is a methyl group, $R_2$ is a methylthio group at the 4-position, $R_3$ is a hydrogen atom and X is an oxygen atom.

11. The benzimidazole derivative according to claim 1, wherein $R_1$ is a methyl group, $R_2$ is a chlorine atom at the 3-position, $R_3$ is a hydrogen atom and X is an oxygen atom.

12. The benzimidazole derivative according to claim 1, wherein $R_1$ is a methyl group, $R_2$ is a methyl group at the 3-position, $R_3$ is a chlorine atom at the 4-position and X is an oxygen atom.

13. The benzimidazole derivative according to claim 1, wherein $R_2$ and $R_3$ are, the same or different, each a $C_1$–$C_8$ alkyl group, a $C_2$–$C_6$ alkenyl group, a $C_2$–$C_6$ alkynyl group, a cyclo($C_3$–$C_6$)alkyl group, a $C_1$–$C_6$ alkoxy group, a $C_2$–$C_6$ alkenyloxy group, a $C_2$–$C_6$ alkynyloxy group, a cyclo($C_3$–$C_6$)alkyloxy group, a $C_1$–$C_6$ alkylthio group, a $C_2$–$C_6$ alkenylthio group, a $C_2$–$C_6$ alkynylthio group, a cyclo($C_3$–$C_6$)alkylthio group, a di($C_1$–$C_6$)alkylamino group, a $C_1$–$C_6$ alkylsulfonyl group, a $C_1$–$C_6$ alkylsulfinyl group, a halo($C_1$–$C_6$)alkyl group, a halo($C_2$–$C_6$)alkenyl group, a halo($C_2$–$C_6$)alkynyl group, a halo($C_1$–$C_6$)alkoxy group, a halo($C_2$–$C_6$)alkenyloxy group, a halo($C_2$–$C_6$)alkynyloxy group, a halo($C_1$–$C_6$)alkylthio group, a halo($C_2$–$C_6$)alkenylthio group, a halo($C_2$–$C_6$)alkynylthio group, a halo($C_1$–$C_6$)alkylsulfonyl group, a halo($C_1$–$C_6$)alkylsulfinyl group, a $C_1$–$C_5$ alkoxy($C_1$–$C_5$)alkyl group, a halo($C_1$–$C_5$)alkoxy($C_1$–$C_5$)alkyl group, a $C_1$–$C_5$ alkylthio($C_1$–$C_5$)alkyl group, a halo($C_1$–$C_5$)alkylthio($C_1$–$C_5$)alkyl group, a $C_1$–$C_5$ alkoxy($C_1$–$C_5$)alkoxy group, a halo($C_1$–$C_5$)alkoxy($C_1$–$C_5$)alkoxy group, a $C_2$–$C_5$ alkenyloxy($C_1$–$C_4$)alkyl group, a $C_2$–$C_5$ alkynyloxy($C_1$–$C_4$)alkyl group, a $C_2$–$C_5$ alkenyloxy($C_1$–$C_4$)alkoxy group, a $C_2$–$C_5$ alkynyloxy($C_1$–$C_4$)alkoxy group, a $C_1$–$C_5$ alkoxy($C_1$–$C_5$)alkylthio group, a $C_1$–$C_5$ alkylthio($C_1$–$C_5$)alkylthio group or $C_1$–$C_5$ alkylthio($C_1$–$C_5$)alkoxy group.

14. The benzimidazole derivative according to claim 1, wherein $R_2$ and $R_3$ are combined together to form a 3,4-methylenedioxy group, a 3,4-difluoromethylenedioxy group, a 3,4-trifluoroethylenedioxy group, a 3,4-trimethylene group or a 3,4-tetramethylene group.

15. The benzimidazole derivative according to claim 1, wherein X is an imino group.

16. An insectical and/or acaricidal composition which comprises as an active ingredient an insecticidally or acaricidally effective amount of a benzimidazole derivative of the formula:

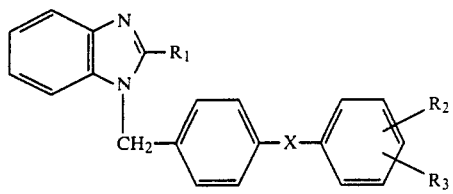

wherein $R_1$ is a hydrogen atom or a lower alkyl group, $R_2$ and $R_3$ are, the same or different, each a hydrogen atom, a halogen atom, a nitro group, a cyano group, a $C_1$–$C_8$ alkyl group, a $C_2$–$C_6$ alkenyl group, a $C_2$–$C_6$ alkynyl group, a cyclo($C_3$–$C_6$)alkyl group, a $C_1$–$C_6$ alkoxy group, a $C_2$–$C_6$ alkenyloxy group, a $C_2$–$C_6$ alkynyloxy group, a cyclo($C_3$–$C_6$)alkyloxy group, a $C_1$–$C_6$ alkylthio group, a $C_2$–$C_6$ alkenylthio group, a $C_2$–$C_6$ alkynylthio group, a cyclo($C_3$–$C_6$)alkylthio group, a di($C_1$–$C_6$)alkylamino group, a $C_1$–$C_6$ alkylsulfonyl group, a $C_1$–$C_6$ alkylsulfinyl group, a halo($C_1$–$C_6$)alkyl group, a halo($C_2$–$C_6$)alkenyl group, a halo($C_2$–$C_6$)alkynyl group, a halo($C_1$–$C_6$)alkoxy group, a halo($C_2$–$C_6$)alkenyloxy group, a halo($C_2$–$C_6$)alkynyloxy group, a halo($C_1$–$C_6$)alkylthio group, a halo($C_2$–$C_6$)alkenylthio group, a halo($C_2$–$C_6$)alkynylthio group, a halo($C_1$–$C_6$)alkylsulfonyl group, a halo($C_1$–$C_6$)alkylsulfinyl group, a $C_1$–$C_5$ alkoxy($C_1$–$C_5$)alkyl group, a halo($C_1$–$C_5$)alkoxy($C_1$–$C_5$)alkyl group, a $C_1$–$C_5$ alkylthio($C_1$–$C_5$)alkyl group, a halo($C_1$–$C_5$)alkylthio($C_1$–$C_5$)alkyl group, a $C_1$–$C_5$ alkoxy($C_1$–$C_5$)alkoxy group, a halo($C_1$–$C_5$)alkoxy($C_1$–$C_5$)alkoxy group, a $C_2$–$C_5$ alkenyloxy($C_1$–$C_4$)alkyl group, a $C_2$–$C_5$ alkynyloxy($C_1$–$C_4$)alkyl group, a $C_2$–$C_5$ alkenyloxy($C_1$–$C_4$)alkoxy group, a $C_2$–$C_5$ alkynyloxy($C_1$–$C_4$)alkoxy group, a $C_1$–$C_5$ alkoxy($C_1$–$C_5$)alkylthio group, a $C_1$–$C_5$ alkylthio($C_1$–$C_5$)alkylthio group or a $C_1$–$C_5$ alkylthio($C_1$–$C_5$)alkoxy group, or $R_2$ and $R_3$ are combined together to form a 3,4-methylenedioxy group, a 3,4-difluoromethylenedioxy group, a 3,4-trifluoroethylenedioxy group, a 3,4-trimethylene group or a 3,4-tetramethylene group and X is an oxygen atom, a sulfur atom, a methylene group, a sulfonyl group, a sulfinyl group or an imino group, and an inert carrier or diluent.

17. An insecticidal and/or acaricidal composition which comprises as an active ingredient an insecticidally or acaricidally effective amount of a benzimidazole derivative according to claim 13.

18. A method for controlling or exterminating insects and/or acarids which comprises applying as the active ingredient an effective amount of the benzimidazole derivative according to claim 1 to the locus where insects and/or acarids propagate.

19. A method for controlling or exterminating insects and/or acarids which comprises applying as the active ingredient an effective amount of the benzimidazole derivative according to claim 13 to the locus where insects and/or acarids propagate.

* * * * *